United States Patent [19]

Sterman et al.

[11] Patent Number: 5,209,731
[45] Date of Patent: May 11, 1993

[54] HAND-HELD GUN FOR INFLATING AND ASPIRATING LARGE VOLUME BALLOONS

[75] Inventors: Wesley D. Sterman, San Francisco; Ronald G. Williams, Menlo Park; Alec A. Piplani, Mountain View, all of Calif.

[73] Assignee: Endovascular Technologies, Inc., Menlo Park, Calif.

[21] Appl. No.: 807,455

[22] Filed: Dec. 13, 1991

[51] Int. Cl.$^5$ .............................................. A61M 29/00
[52] U.S. Cl. ........................................ 604/97; 604/99; 604/131; 222/340; 222/391
[58] Field of Search .................... 604/96–103, 604/70, 72, 131, 134, 135, 136, 93, 94; 222/336, 335, 340, 391

[56] References Cited

U.S. PATENT DOCUMENTS

| | | | |
|---|---|---|---|
| 2,892,457 | 6/1959 | Sturtz | 222/391 |
| 3,122,280 | 2/1964 | Goda | 222/340 |
| 4,333,459 | 6/1982 | Becker | 604/135 |
| 4,808,165 | 2/1989 | Carr | 604/97 |
| 4,840,294 | 6/1989 | Ernst | 222/391 |
| 4,976,725 | 12/1990 | Chin et al. | 604/97 |

Primary Examiner—John D. Yasko
Assistant Examiner—William Lewis

[57] ABSTRACT

Hand-held gun for inflating and deflating large volume balloons by the use of a syringe having a barrel and a syringe plunger having a head and slidably mounted in the barrel. The gun is provided with a handle adapted to be grasped by the hand. A housing is carried by the handle and is adapted to receive and retain the barrel of the syringe. A plunger rod is provided which has proximal and distal extremities and is slidably mounted in the handle for movement in a direction parallel to the movement of the syringe plunger between forward and rearward positions. A sleeve is secured to the proximal extremity of the plunger rod and extends coaxially for at least a portion of the plunger rod. A coil spring is mounted on the plunger rod for yieldably urging the plunger rod in a direction axially of the plunger rod toward the rearward position. A plate is secured to the sleeve and is adapted to be removably secured to the head of the syringe plunger. A gripper is pivotally mounted on the handle and engages the plunger rod for progressively advancing the plunger rod towards a forward position against the force of the coil spring to advance the syringe plunger in the barrel for causing an inflating liquid to be discharged from the barrel for inflation of the balloon. A trigger is pivotally mounted on the handle for releasing the plunger rod from a forward position to permit the spring means to return the plunger rod to a rearward position and to carry with it the syringe plunger to aspirate fluid from the balloon to cause deflation of the balloon.

4 Claims, 1 Drawing Sheet

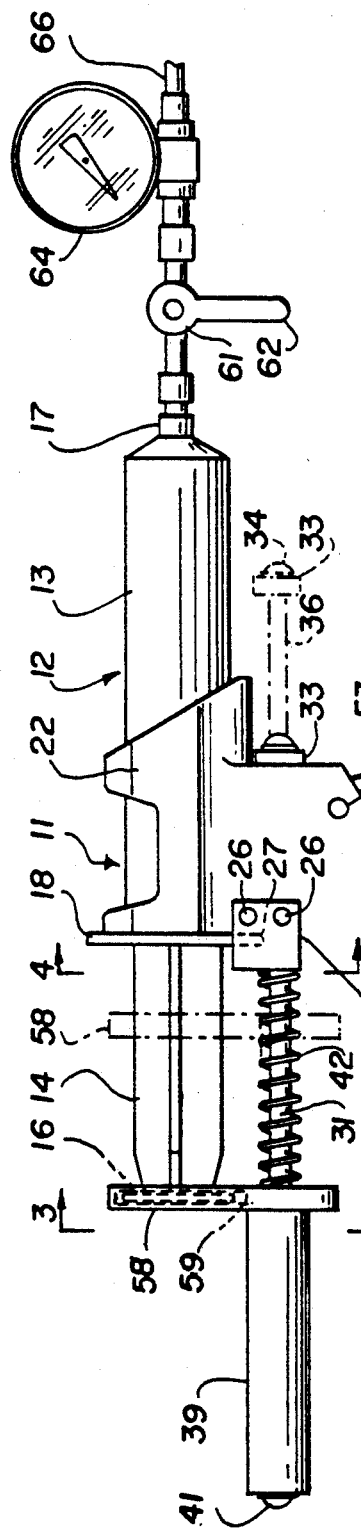
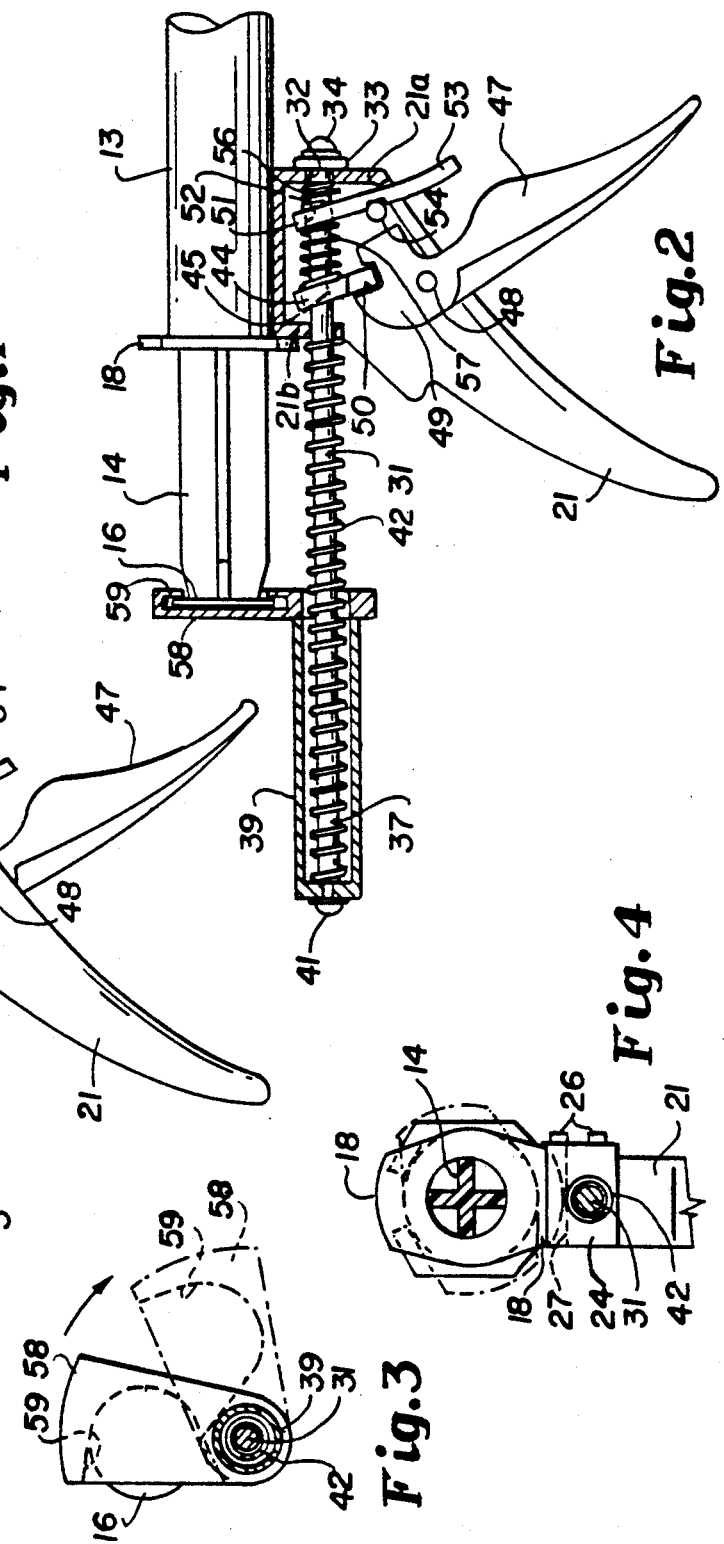

HAND-HELD GUN FOR INFLATING AND ASPIRATING LARGE VOLUME BALLOONS

This invention relates to a hand-held gun for inflating and aspirating large volume balloons and more in particular to such a hand-held gun for use in medical procedures.

Hand-held guns have heretofore been provided for inflating balloons. One such gun is a syringe injection gun manufactured and sold by Applied Medical Technology, 6551 Brecksville Road, Independence, Ohio 44131. With such a device it has been found it is very difficult to aspirate or deflate a large volume balloon particularly when the balloon is connected to a small lumen catheter. In the past with such a device it has been necessary to remove the syringe from the gun or disconnect the gun mechanism from the syringe and then utilizing the hand to pull out the plunger of the syringe in an attempt to hand aspirate the balloon. There is therefore a need for a new and improved hand-held gun which can be used for inflating and deflating large volume balloons which overcomes the above-named disadvantages.

In general, it is an object of the present invention is to provide a hand-held gun for inflating and deflating large volume balloons.

Another object of the invention is to provide a gun of the above character which utilizes a large syringe.

Another object of the invention is to provide a hand-held gun of the above character in which the syringe can be readily inserted and removed.

Another object of the invention is to provide a hand-held gun of the above character in which the balloon can be progressively inflated.

Another object of the invention is to provide a hand-held gun of the above character which permits rapid deflation or aspiration of the balloon.

Additional objects and features of the invention will appear from the following description in which the preferred embodiment is set forth in detail in conjunction with the accompanying drawing.

FIG. 1 is a side elevational view of a hand-held gun incorporating the present invention for inflating and deflating large volume balloons.

FIG. 2 is a partial cross-sectional view of a portion of the hand-held gun shown in FIG. 1.

FIG. 3 is a cross-sectional view taken along the line 3—3 of FIG. 1.

FIG. 4 is a cross-sectional view taken along the line 4—4 of FIG. 1.

In general, the hand-held gun for inflating and deflating large volume balloons uses a syringe having a barrel and a syringe plunger slidably mounted in the barrel. The syringe 12 is of a size so that a large volume balloon having a size ranging from 20 to 50 cc can be filled. For example, the syringe 12 can have a volume of 2 fluid ounces or 60 cc. The gun consists of a handle which is adapted to be grasped by the hand of the user. Housing means is provided which is mounted on the handle and is adapted to receive and retain the barrel of the syringe. A plunger rod is provided which has proximal and distal extremities and is slidably mounted on said handle for movement in a direction parallel to the direction of movement of the syringe plunger between forward and rearward positions. A sleeve is secured to the proximal extremity of the plunger rod and extends coaxially for at least a portion of the plunger rod. Yieldable spring means is mounted on the plunger rod which yieldably urges the plunger rod in a direction axially of the plunger rod towards the rearward position. Means is secured to the sleeve and is adapted to be secured to the syringe plunger. Lever means is pivotally mounted on the handle and engages the plunger rod for progressively advancing the plunger rod towards the forward position against the force of the yieldable means to thereby advance the syringe plunger in the barrel for causing fluid to be discharged from the barrel for inflation of a balloon. Trigger means is pivotally mounted on the handle for releasing said plunger rod from a forward position to permit said yieldable spring means to return said plunger rod to a rearward position whereby said syringe plunger is also moved to a rearward position to aspirate fluid from the balloon to cause deflation of the balloon.

More in particular as shown in FIGS. 1 through 4 of the drawings, the hand-held gun 11 for inflating and deflating large volume balloons is particularly adapted to be used in conjunction with a large volume syringe 12 of a conventional type which is provided with a barrel 13 with having a plunger 14 slidable axially within the barrel 13. The plunger 14 is provided with a head piece 16 extending perpendicular to the direction of axial movement of the plunger 14. The syringe 12 is provided with a Luer-type outlet fitting 17. The barrel 13 of the syringe 12 is provided with a flange 18.

The gun 11 is provided with a handle 21 which is of a size that is adapted to fit into the palm of the human hand and be grasped by the fingers of the same hand. The handle 21 can be formed of a suitable material such as metal or plastic. The handle 21 is provided with parallel spaced apart, downwardly depending portions 21a and 21b (see FIG. 2).

Housing means is provided and is formed integral with the handle which is adapted to receive the barrel 13 of the syringe 12. As shown therein, the housing means is in the form of a sleeve 22 formed integral with the handle.

Means is provided for engaging the flange 18 of the barrel 13 of the syringe 12 to limit its forward or rearward movement in the sleeve 22. This means consists of a bracket 24 which is secured to the handle 21 by a suitable means such as screws 26. The bracket 24 is provided with a rectangular recess 27 which is adapted to receive the flange 18 therein and to prevent either forward or rearward movement of the syringe 13 with respect to the sleeve 22 and the handle 21.

An elongate plunger rod 31 is slidably mounted in the handle 21 for movement between forward and rearward directions along a longitudinal axis which is parallel to the axis of the sleeve 22 and the barrel 13 of the syringe 12 mounted therein. As shown particularly in FIG. 2, the plunger rod 31 is slidably mounted in a hole 32 in the downwardly depending portion 21a of the handle 21 and extends through a rubber grommet 33. The plunger rod 31 is provided with an enlarged head 34 to prevent it from moving in a rearward direction through the rubber grommet 33 and the hole 32. The plunger rod 31 is provided with a distal or forward extremity 36 and a rearward or proximal extremity 37. A cylindrical sleeve 39 which has one end open is coaxially mounted on the proximal extremity 37 of the plunger rod 31. It is secured thereto by suitable means such as a screw 41 extending through the sleeve and threaded into the proximal extremity of the plunger rod 31.

A helical coil spring 42 is mounted coaxially on the plunger rod 31 and extends from the proximal extremity within the cylindrical sleeve 39 and to the downwardly depending portion 21b of the handle 21 to apply a spring force yieldably urging the plunger rod 31 in a rearward direction.

Means is carried by the handle for progressively advancing the plunger rod 31 against the force of the yieldable coil spring 42 and consists of a gripper member 44 which is provided with an angled hole 45 therein through which the plunger rod 31 extends. The gripper member 44 is adapted to be actuated by a lever arm 47 pivotally mounted on a pin 48 mounted in the handle 21. The lever arm 47 is provided with a jaw 49 having a recess 50 therein which receives the lower extremity of the gripper member 44. Another gripper member 51 is provided which is positioned ahead of the gripper member 44 and also is provided with an angled hole 52. The gripper member 51 is provided with a trigger 53 which is formed integral therewith. The trigger 53 is pivotally mounted on a pin 54 mounted in the handle 21 in close proximity to the level arm 47. A spring 56 is mounted on the rod 31 between the depending portion 21a and the gripper member 51. Another spring 57 is mounted on the rod 31 between gripper 51 and the gripper member 44. As can be seen from FIGS. 1 and 2, the handle 21 is adapted to be engaged by the palm of the hand whereas the fingers of the same hand can be utilized for engaging the lever arm 47 and the trigger 53.

Means is provided for securing the proximal extremity of the plunger rod 31 to the head piece 16 of the plunger 14 of the syringe 12 and consists of a plate 58 which is secured to the sleeve 39 by suitable means such as welding. The plate 58 is provided with a semicircular recess 59 which is adapted to receive the head piece 16. Thus as shown in FIG. 3, the plate 56 can be swung into a position so that it engages the head piece 16 so that the plunger 14 moves with the sleeve 39 as the sleeve 39 is moved axially with the plunger rod 31. Also the plate 56 can be swung to an out-of-the-way position to permit the syringe 12 to be removed from the gun.

A stopcock 61 which is provided with a handle 62 is mounted on the fitting 17. A pressure gauge 64 is mounted on the stopcock 61. A flexible tube 66 is connected to the gauge 64 for supplying fluid from the syringe 12 to a large volume balloon (not shown) or for aspirating fluid from the large volume balloon.

Operation and use of the hand-held gun for inflating and deflating large volume balloons may be briefly described as follows. Let it be assumed that a surgical procedure is under way in which it is desired to inflate and deflate a large volume balloon having a capacity of 30 cc. This can be accomplished by connecting the tube 66 to the catheter used for inflating the balloon. Let it also be assumed that the syringe 12 has been filled with a suitable fluid or liquid such as a conventional radiopaque solution reduced by 50% by water to be used for inflating the balloon. With the plunger rod 31 being in the position shown in FIG. 1, in an extreme rearward position, let it be assumed that it is now desired to inflate the balloon. The stopcock lever 62 is moved to open the valve to permit inflating medium to be discharged from the barrel. This is accomplished by the physician grasping the handle 2 in the palm of the hand and utilizing the fingers of the same hand to repeatedly pull rearwardly the lever 47 to cause progressive advancement of the rod 31 as the gripper member 44 is urged forwardly against the force of the spring 57 to cause gripper 51 to be advanced against the force of the spring 56 to release the rod 31 to permit rod 31 to be advanced by the gripper 44. Release of the lever 47 permits spring 56 to urge the gripper 56 to grasp the rod 31 to prevent its return by coil spring 42. The spring 57 returns the gripper 44 so that it can grip the next successive portion of the plunger rod 31 when the lever 47 is again actuated to advance the plunger rod 31 in an axial direction parallel to the barrel 13 as shown in broken lines in FIG. 1. As the gripper member 44 advances the rod 31, the gripper member 51 will engage the rod to prevent it from being pushed rearwardly under the force of the coil spring 42. Thus it can be seen that the gripper member 44 progressively advances the plunger rod 31 while the other gripper member 51 engages the plunger rod to prevent it from slipping rearwardly until the gripper member 44 obtains another grip on the rod and advances it forwardly. This progressive advancement of the plunger rod 31 can continue until a sufficient amount of the inflating medium has been discharged from the barrel 13 into the tubing 66 to inflate the balloon and to create a predetermined pressure in the balloon as determined by the measurement made by the pressure gauge 64. As soon as the desired pressure has been reached in the balloon as determined by reading the gauge 64, it is no longer necessary to further advance the plunger rod 31.

Now let it be assumed that it is desired to rapidly deflate the balloon which has been inflated. This is accomplished by a finger of the hand grasping the trigger level 53 while the same hand engages the lever 47 to advance the gripper member 44 to a position so that when the plunger rod 31 is released by the gripper member 51 by operation of the trigger 53, the plunger rod 31 is urged rearwardly under the force of the spring 42 to bring with it the plunger 14 to thereby rapidly aspirate fluid from the balloon and to thereby deflate the balloon.

If desired, the balloon can then again be rapidly reinflated by repeatedly operating the lever arm 47 in the manner hereinbefore described to discharge inflating medium from the barrel 13 into the balloon. Deflation can also thereafter be made to occur by pressing the trigger 53 by another finger of the hand.

From the foregoing it can be seen that there has been provided a hand-held gun which can be utilized for rapidly inflating and deflating large volume balloons. The large volume syringe which is mounted in the gun can be readily removed from the gun and replaced when necessary.

What is claimed is:

1. In a hand-held gun for inflating and deflating large volume balloons by the use of a syringe having a barrel and a syringe plunger having a head and slidably mounted in the barrel, a handle adapted to be grasped by the hand, housing means carried by the handle adapted to receive and retain the barrel of the syringe, a plunger rod having proximal and distal extremities slidably mounted in said handle for movement in a direction parallel to the movement of the syringe plunger between forward and rearward positions, a sleeve secured to the proximal extremity of the plunger rod and extending coaxially for at least a portion of the plunger rod, spring means mounted on the plunger rod for yieldably urging said plunger rod in a direction axially of the plunger rod toward the rearward position, means secured to the sleeve and adapted to be removably secured to the head of the syringe plunger, gripper means pivotally mounted on said handle and engaging said plunger rod for progressively advancing said plunger rod towards a forward position against the force of the spring means to advance said syringe plunger in the barrel for causing an inflating liquid to be discharged from the barrel for inflation of the balloon, and trigger means pivotally mounted on the handle for releasing said plunger rod from a forward position to permit said spring means to return said plunger rod to a rearward position and to carry with it the syringe plunger to aspirate fluid from the balloon to cause deflation of the balloon.

2. A gun as in claim 1 wherein said spring means extend coaxially into said sleeve.

3. A gun as in claim 1 wherein said means secured to said sleeve include a plate secured to said sleeve and having a recess therein adapted to receive said head of the syringe plunger.

4. A gun as in claim 3 wherein said plate is movable into and out of engagement with said head of said syringe plunger.

* * * * *